United States Patent [19]

Lautz

[11] Plant 4,824

[45] Feb. 16, 1982

[54] EARLY RIPENING HARALSON APPLE—LAUTZ CULTIVAR

[75] Inventor: Louis R. Lautz, La Crosse, Wis.

[73] Assignee: Bailey Nurseries, Inc., St. Paul, Minn.

[21] Appl. No.: 127,963

[22] Filed: Mar. 6, 1980

[51] Int. Cl.[3] ..... A01H 5/03
[52] U.S. Cl. ..... Plt./34
[58] Field of Search ..... Plt./34

*Primary Examiner*—Robert E. Bagwill

*Attorney, Agent, or Firm*—Burns, Doane, Swecker & Mathis

[57] ABSTRACT

A new and distinct variety of apple tree is provided which is believed to be a whole tree mutation or sport of the regular Haralson apple variety. The new variety is distinguished from the regular variety by the ability to form apples which (1) ripen earlier, (2) are more uniformly red in color with the absence of striping, (3) are resistant to russeting, and (4) are slightly sweeter in taste.

1 Drawing Figure

SUMMARY OF THE INVENTION

The Haralson variety is well known and was introduced commercially in 1923 following its origination at the University of Minnesota Fruit Breeding Farm, Excelsior, Minn. Trees of the Haralson variety have been grown and observed by me for a number of years at the Lautz Orchard, La Crescent, Minn. The new and distinct variety of the present invention is believed to be a whole tree mutation of the original Haralson variety.

During approximately 1963 I observed a single tree growing among the Haralson variety at the Lautz Orchard, La Crescent, Minn., which appeared to be exhibiting distinctive fruit characteristics. Since the tree in question had been planted in an area having less than optimum soil conditions because of the presence of rock which had previously been used to fill an erosion ditch, it was not immediately apparent whether the distinctive fruit appearance could be attributed solely to the growing conditions being encountered by the tree in question.

Further observations of the tree during succeeding years revealed that the observed distinctive fruit characteristics such as (1) a propensity for earlier ripening, (2) a more uniformly red color in the absence of striping, (3) a resistance to russeting, and (4) a slightly sweeter taste, were indeed consistently displayed. During approximately 1967 the tree in question was asexually reproduced by grafting scion wood onto young Hibernal stocks which were grown in a nearby area of the same orchard where there was no question concerning the quality of the soil conditions. These and subsequent asexual reproductions have confirmed that the distinctive characteristics of the new variety come true to form and are established and transmitted through succeeding propagations.

This new variety has been named the Lautz cultivar of the Haralson apple.

BRIEF DESCRIPTION OF THE PHOTOGRAPHS

The fruit illustrated in the photographs was produced at La Crescent, Minn., and is depicted in color as nearly true as possible to make the same in a color illustration of this character.

DETAILED DESCRIPTION OF THE NEW VARIETY

Figure 1:
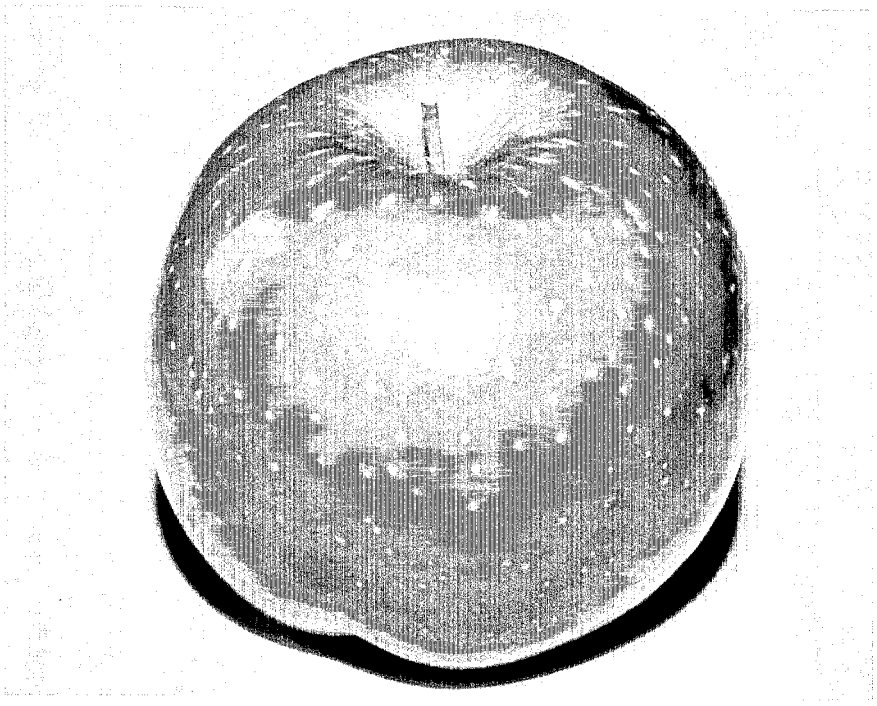
FIG. 1 illustrates a single apple of the new variety which bears the more uniform red coloration in the absence of striping and russeting.
Figure 2:
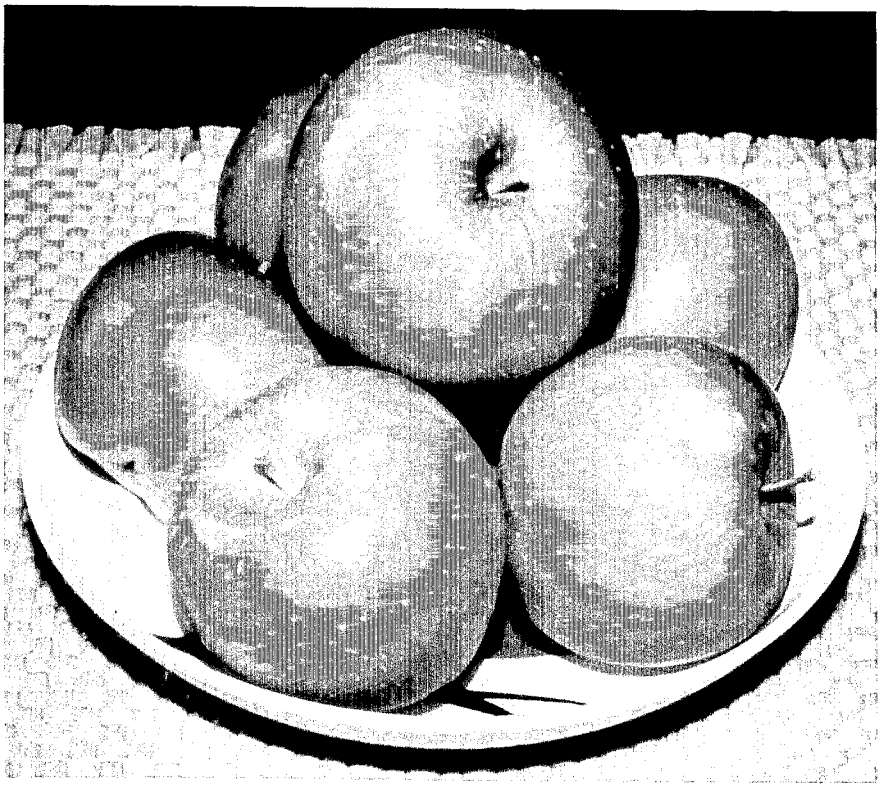
FIG. 2 illustrates a plurality of apples of the new variety which bear the more uniform red coloration in the absence of striping and russeting.

The trees described were grown at La Crescent, Minn.

Unless otherwise stated the new variety has characteristics which are substantially identical to those of the regular Haralson apple variety (non-patented). Color terminology used herein is to be accorded its usual dictionary significance.

The fruit of the new variety commonly is ready for harvesting during the last week of September when grown at La Crescent, Minn., and approximately two weeks prior to that of the regular Haralson apple variety grown at the same location. Such early ripening characteristic should enable the new variety to be grown farther north where the growing season is shorter.

The fruit of the new variety is of a more uniform dark red appearance than that of the regular Haralson variety. The striping which is commonly present on the fruit of the regular Haralson variety is absent, and the skin is more uniformly overlaid with dark red coloration (as illustrated). Large dots are present as on the regular Haralson variety.

No russeting has been observed upon the fruit of the new variety to date. It accordingly is assumed that resistance to russeting is an inherent characteristic of the new variety. Such resistance has been exhibited even when considerable russeting is present upon fruit of adjacently grown trees of the regular Haralson variety.

It further has been found that the taste of the fruit of the new variety is slightly sweeter than that of the regular Haralson variety although it still has the familiar tart taste commonly associated with the regular Haralson variety.

I claim:

1. A new and distinct variety of apple tree which originated as a whole tree mutation of the Haralson apple variety, substantially as illustrated and described, characterized by its general similarity to the Haralson apple tree, but being distinct therefrom by the ability to form apples which (1) ripen earlier, (2) are more uniformly red in color with the absence of striping, (3) are resistant to russeting, and (4) are slightly sweeter in taste.

* * * * *